United States Patent [19]

Smith

[11] 4,085,150
[45] Apr. 18, 1978

[54] PROCESS FOR THE ORTHO ALKYLATION OF PHENOLS IN THE PRESENCE OF A COPPER-ZINC-ALUMINUM MIXED OXIDE CATALYST

[75] Inventor: William Edward Smith, Schenectady, N.Y.

[73] Assignee: General Electric Company, Pittsfield, Mass.

[21] Appl. No.: 676,502

[22] Filed: Apr. 13, 1976

[51] Int. Cl.$^2$ ............................................. C07C 39/06
[52] U.S. Cl. ........................... 260/621 R; 260/619 R; 260/620; 260/624 C
[58] Field of Search ........... 260/624 C, 624 R, 621 R, 260/620, 619 R

[56] References Cited

U.S. PATENT DOCUMENTS

| 2,448,942 | 9/1948 | Winkler et al. | 260/621 R |
| 2,793,239 | 5/1957 | Toland | 260/671 R |
| 3,716,589 | 2/1973 | Kotanigawa et al. | 260/621 K |

*Primary Examiner*—James O. Thomas, Jr.
*Assistant Examiner*—Werren B. Lone
*Attorney, Agent, or Firm*—William F. Mufatti

[57] ABSTRACT

A process for selectively ortho-alkylating a phenolic compound which comprises reacting the phenolic compound with an alkanol in the presence of a copper-zinc-aluminum mixed oxide catalyst.

3 Claims, No Drawings

PROCESS FOR THE ORTHO ALKYLATION OF PHENOLS IN THE PRESENCE OF A COPPER-ZINC-ALUMINUM MIXED OXIDE CATALYST

This invention is directed to a process for selectively ortho-alkylating a phenolic compound which comprises reacting the phenolic compound with an alkanol in the presence of a copper-zinc-aluminum mixed oxide catalyst.

BACKGROUND OF THE INVENTION

It is well known in the art to alkylate phenols having at least one unsubstituted ortho position. Many prior art processes have been disclosed as being non-selective and indiscriminate in regard to the nature of the products that are formed. Winkler et al., U.S. Pat. No. 2,448,942, for example, discloses a process for the preparation of penta-substituted phenols. The Winkler et al patent mentions that one may employ either alcohol or methyl ether in the vapor phase using various metal oxides such as aluminum oxide, barium oxide, manganese oxide, magnesium oxide, calcium oxide, etc. as the catalyst. Alumina is the preferred catalyst. The Winkler et al process, however, is somewhat indiscriminate and lacks specificity for ortho-alkylation to the relative exclusion of alkylation in the meta- and para- positions.

Winkler et al. teach that the reaction is carried out at superatmospheric pressures at temperatures in the range of 300° C. to about 450° C. However, temperatures of about 430° C have been noted, e.g., in Hamilton, U.S. Pat. No. 3,446,856, to cause a decrease in the yield of alkylated product. When phenol and methanol are reacted at temperatures above 450° C, Hamilton teaches that the production of hexamethyl benzene, a non-phenolic product, is favored. For reactions of methanol with phenol, xylenol or cresol, Hamilton stated that a temperature of about 350° to 430° C is favored in order to obtain high yields of alkylated product, while temperatures below 350° C increase the yield of ether byproducts. Temperatures of above 450° C and superatmospheric pressures cause decomposition of the reactant and favor the production of unwanted materials. The Hamilton process was based on the discovery that magnesium oxide was a selective ortho-alkylation catalyst that was useful at atmospheric pressure at a defined temperature range.

U.S. Pat. Nos. 3,707,569 and 3,751,488 are based respectively, on the discoveries that certain tellurium-containing compounds and molybdic acid salts are useful as selective ortho-alkylation catalysts. Further, U.S. Pat. No. 3,764,630 describes a method for selectively alkylating a phenol compound with an alkanol in the presence of water and a catalytically active compound such as molybdenum oxide and alkali metal, alkaline earth metal, lead, bismuth and ammonium salts of molybdic acid in admixture with magnesium oxide. Also, U.S. Pat. No. 3,843,606 discloses a catalyst which is porous magnesium oxide powder bonded with an inert organic cellulosic polymeric binder for use in selective alkylation of phenols. Lastly, U.S. Pat. No. 3,873,628 discloses mixtures of magnesium oxide and manganese sulfate as useful catalysts for ortho-alkylation of phenols. These patents are incorporated herein by reference.

Ortho-alkylated phenols have valuable properties. They are particularly useful as the starting material for the manufacture of polyarylene ethers such as polyphenylene oxide, a valuable thermoplastic resin disclosed and claimed, for example, in A. S. Hay's U.S. Pat. No. 3,306,875.

DESCRIPTION OF THE INVENTION

In copending application of William E. Smith, Ser. No. 676,503, filed Apr. 13, 1976, titled "A PROCESS FOR THE SELECTIVE ORTHO-ALKYLATION OF A PHENOL IN THE PRESENCE OF A COPPER-CHROMIUM CATALYST" and assigned to the same assignee as the present invention, there is disclosed a process by which phenols and alkanols can be converted to the ortho-alkylated phenols with high selectivity and under mild conditions in the presence of a copper-chromium catalyst. The present invention is concerned with a process for selectively ortho-alkylating a phenolic compound which comprises reacting the phenolic compound with an alkanol in the presence of a copper-zinc-aluminum mixed oxide catalyst, said process being characterized by high selectivity with respect to both phenol and methanol.

The phenolic compound is of the general formula:

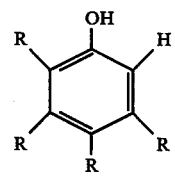

wherein each R is a monovalent substituent selected from the group consisting of hydrogen, alkyl of 1 to 12 carbon atoms, aryl of 6 to 12 carbon atoms and alkaryl of 7 to 12 carbon atoms. Examples of these substituents include methyl, ethyl, n-propyl, phenyl, o-methylphenyl, p-methylphenyl, 2,6-xylyl, and the like. Especially useful starting materials are phenol, o-cresol, m-cresol, p-cresol, o-phenylphenol and 3,5-xylenol. The preferred embodiment of the process is carried out using phenol, ortho cresol, or a mixture of the two as the phenolic starting material.

Suitable alkanols may be represented by the formula:

R'OH wherein R' is an alkyl radical of up to about 12 carbon atoms, straight chain or branched chain. Illustrative alcohols are those wherein R' is methyl, ethyl, n-propyl, i-propyl, n-butyl, hexyl, octyl, 2-ethylhexyl, decyl or dodecyl. A preferred alkanol is methanol.

In order to obtain the maximum yield of ortho-alkylated products, it is preferred to use at least 0.5 mole of alkanol, and preferably from 1 to 3 moles of alkanol for each ortho position hydrogen in the phenolic compound to be alkylated. For example, if phenol is to be methylated to produce a maximum yield of 2,6-xylenol (2,6-dimethylphenol), it is preferred to use at least 2 moles and especially preferred to use from 2 to 6 moles of methanol for each mole of phenol. Of course, if the phenolic compound is already mono-substituted in one of the ortho positions, maximum yields will be obtained with at least one mole of alkanol, e.g., methanol, per mole of phenolic compound, e.g., ortho cresol.

The catalysts of the instant invention are copper-zinc-aluminum mixed oxide compositions. The proportions of the three metals can be individually varied over the range of from about 3 mole percent to about 90 mole percent of the overall composition. The preferred proportions are from about 6 to about 30 mole percent copper, from about 5 to about 50 mole percent zinc, and from about 20 to about 80 mole percent aluminum, as the oxides. In addition, the catalysts can contain inert constituents, binders, etc.

The catalysts of the instant invention can be prepared by methods well known in the art, such as, for example, coprecipitation or pyrolysis of oxide precursors.

The catalyst is preferably used in the form of a bed through which the reactants are passed in the vapor phase. Preferred pressures are in the range from about atmospheric to about 5 atmospheres.

The instant process is carried out at a temperature of at least 185° C. The optimum alkylation temperature is in the range of from 185° C. to about 350° C.

The instant process may be carried out using a variety of reactors with varying flow rates of the reactants, varying vapor space velocities of the reactants and length of the catalyst bed. Tubular reactors, such as a glass or a metal tube filled with a bed of the catalyst, may be employed. The reactor is heated with conventional means either by surrounding the reactor with an electrical heater, a heated gas, or a fused salt bath, liquid metal, etc., which can be conveniently maintained at reaction temperature by the use of immersion type electrical heaters. Alternatively, a fluid bed reactor may be used. The alkylation reaction is exothermic and, therefore, the heat of reaction can be utilized to maintain the catalyst bed at the proper reaction temperature.

The techniques are conventional and reference is made to the above-mentioned patents.

In carrying out an alkylation in accordance with the invention, any one or a mixture of phenols having an ortho hydrogen together with an alkanol may be vaporized and passed through a reactor heated to a temperature of at least 185° C. containing the copper-zinc-aluminum catalyst of the invention. The alkanol can be mixed with the phenol to form a solution which is then vaporized or separate streams of the two reactants may be fed to the same or separate vaporizers and then to said reactor. Also, the reactants may be passed through the catalyst bed with a hydrogen carrier gas, for example.

The vapors issuing from the reactor are condensed in the usual fashion and the products separated in the usual fashion, for example, by crystallization, distillation, etc.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE 1

A vertical hot tube reactor (20 mm ID × 30 cm effective length) was constructed from heavy wall glass, with 24/40 male and female joints. Vigreaux points were indented just above the male joint to support catalyst pellets. Thermocouple leads were fastened into three other Vigreaux indentations at points along the length. Three 4 ft. × 1 in. Briskheat glass insulating heating tapes were wound onto the tube, covered with glass wool and glass tape, and connected to separate variable transformers. The tube exit was connected by a gooseneck (also heated) to an efficient condenser and collection vessel. A three-necked flask served as the evaporator, with the reactants added through a side neck by a syringe pump.

The reactor was charged with 70 cc (72 grams) of Girdler G66C low temperature CO conversion catalyst (⅛ × ¼ in. dia. tablets composed of 26% Cu, 44% Zn and 10% Al, the remainder being oxygen). The bed was activated by heating under a hydrogen-nitrogen stream, with care taken to control the exotherm (maximum temperature 300° C).

The reactor temperature was maintained at 300° C while a methanol-phenol mixture (5:1 molar ratio) was passed into the evaporator at 36 ml/hr. (LHSV=0.5) with a 70 ml/min. hydrogen carrier. The steady state effluent had a phenolic composition of 14.3% phenol, 35.4% o-cresol, 50.1% 2,6-xylenol and 0.2% mesitol (2,4,6-trimethylphenol). Not more than traces of anisole products could be detected. The methanol selectivity, as determined by $13_C$ nmr analysis of the effluent, was 40%.

The comparative data for a series of methylations using representative catalysts of the instant invention as well as copper-zinc and copper-aluminum catalysts are given in Table I.

TABLE I

Catalysts for Phenol Methylation
5:1 Methanol-Phenol, LHSV = 0.5

| Oxides | T °C | % Phenol | % o-Cresol | % 2,6-Xylenol | % 2,4,6- | Methanol Selectivity % |
|---|---|---|---|---|---|---|
| Cu/Zn[a] (1.0:2.0) | 300 | 26.1 | 47.9 | 26.0 | — | 25 |
| Cu/Zn/Al[b] (1.0:1.6:0.9) | 300 | 14.3 | 35.4 | 50.1 | 0.2 | 40 |
| Cu/Zn/Al (1.0:0.5:4.2) | 290 | 18.0 | 22.5 | 58.2 | 1.3 | 55 |
| Cu/Zn/Al (1.0:0.5:4.2) (60-40 phenol /o-cresol) | 270 | 14.1 | 29.8 | 55.7 | 0.4 | 60 |
| Cu/Al[c] (1.0:2.0 | 300 | 12.2 | 24.8 | 49.7 | 3.1 | — |

[a]Evolved gas $CO/CO_2/CH_4$ (83:42:1).
[b]Evolved gas $CO/CO_2/CH_4$ (137:58:1).
[c]About 10% conversion to anisoles and more highly methylated products.

As indicated by the data in Table I, the catalysts of the instant invention are superior to both the copper-zinc and copper-aluminum oxide catalysts for the selective orthomethylation of phenol. The presence of the aluminum oxide component results in significantly increased activity and efficiency with respect to methanol selectivity with essentially no decrease in phenol selectivity. Surprisingly, even with the higher level of aluminum oxide incorporation, the tendency toward formation of anisoles and more highly methylated products (e.g., hexamethylbenzene) characteristic of the copper-aluminum system are not evident.

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A process for the selective ortho-alkylation of a phenolic compound of the general formula:

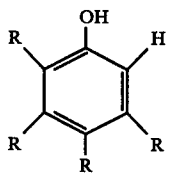

wherein each R is a monovalent substituent selected from the group consisting of hydrogen, alkyl of 1 to 12 carbon atoms, aryl of 6 to 12 carbon atoms and alkaryl of 7 to 12 carbon atoms, the process comprising reacting at a temperature of from 185° C to about 350° C in the presence of a copper-zinc-aluminum mixed oxide catalyst said phenolic compound with an alkanol of 1 to about 12 carbon atoms.

2. A process as defined in claim 1 wherein each R is hydrogen.

3. A process as defined in claim 1 wherein the alkanol is methanol.

* * * * *